United States Patent
Baxendale et al.

(10) Patent No.: US 7,824,689 B2
(45) Date of Patent: Nov. 2, 2010

(54) CHICKEN ASTROVIRUS TYPE 2

(75) Inventors: William Baxendale, Huntingdon (GB); Teshome Mebatsion, Salisbury, MD (US)

(73) Assignee: Intervet International B.V., Boxmeer (NL)

( * ) Notice: Subject to any disclaimer, the term of this patent is extended or adjusted under 35 U.S.C. 154(b) by 610 days.

(21) Appl. No.: 10/527,767

(22) PCT Filed: Sep. 15, 2003

(86) PCT No.: PCT/EP03/10265

§ 371 (c)(1),
(2), (4) Date: Sep. 12, 2005

(87) PCT Pub. No.: WO2004/027053

PCT Pub. Date: Apr. 1, 2004

(65) Prior Publication Data

US 2006/0147464 A1     Jul. 6, 2006

(30) Foreign Application Priority Data

Sep. 18, 2002   (EP) .................................. 02078837

(51) Int. Cl.
*A61K 39/12*        (2006.01)

(52) U.S. Cl. ........................................ 424/204.1; 435/5
(58) Field of Classification Search ....................... None
See application file for complete search history.

(56) References Cited

U.S. PATENT DOCUMENTS 6,086,892 A * 7/2000 Cook ....................... 424/222.1

OTHER PUBLICATIONS

Koci et al., Avian astroviruses, Avian Pathology, 2002, vol. 31, pp. 213-227. See IDS.*
Imada et al., Avian Nephritis Virus (ANV) as a New Member of the Family Astrovirudae abd Construction of Infectious ANV cDNA, Journal of Virology, Sep. 2000. vol. 74, No. 18, pp. 8487-8493. See IDS.*
Koci, M.D. et al. "Avian astroviruses" Avian Pathology (Jun. 2002), V31, N3, p. 213-227, XP-001148703.
Imada, T., et al. "Avian Nephritis Virus (ANV) as a New Member of the Family Astroviridae . . ."Journal of Virology (Sep. 2000) V74, N18, p. 8487-8493, XP002231721.

* cited by examiner

*Primary Examiner*—Ali R. Salimi
(74) *Attorney, Agent, or Firm*—William M. Blackstone

(57) ABSTRACT

The present invention provides a new chicken astrovirus (CAstV). This chicken astrovirus (CAstV-2) is immunologically distinct from known avian astroviruses and can be used to prepare vaccines.

8 Claims, No Drawings

CHICKEN ASTROVIRUS TYPE 2

The present invention is concerned with a chicken astrovirus type 2, a cell culture infected with such a virus as well with a vaccine comprising this virus.

A number of viruses have been associated with enteric disease and growth retardation in chickens and turkeys. In the case of chickens, the virus included our reticulo-endotheliosis virus, reoviruses, Marek's Disease virus, chick anaemia virus, a number of enteroviruses, enterovirus-like viruses, avian encephalomyelitis (AE) virus and avian nephritis virus (ANV), an astrovirus.

Astroviruses are small round, non-enveloped, viruses with a typical diameter of 28-30 nm and harbouring a positive stranded RNA genome. Astroviruses are distinct from other small round viruses (SRVs), such as parvoviruses, circoviruses, picornaviruses and caliciviruses, for example, in respect of their respective, characteristic morphological structures visible by electron microscopy.

The family of Astroviridae (see Fields Virology, eds.: B. N. Fields et al., 1996, Chapter 26) is divided into two genera, i.e. mammalian astroviruses and avian astroviruses, the latter being extensively reviewed by Koci and Schultz-Cherry In Avian Pathology 31, 213-227, 2002. In particular, this document reviews the characterising genome organization and molecular biology of (avian) astroviruses and provides a sequence analysis of the astrovirus open reading frames.

Turkey astroviruses have been associated with diarrhoea and increased mortality in turkey poults. Two types of turkey astrovirus (TastV) have been identified, TastV-1 and TastV-2, but these turkey astroviruses have been found to be genetically and immunologically distinct.

Avian nephritis virus (ANV) isolated from chickens by Yamaguchi, et al in 1979 (Avian Diseases 23, 571-581) has now been (re-)classified as an astrovirus following the complete sequencing of the viral genome (Imada et al., J. Virol. 74, 8487-8493, 2000). This virus is associated with mild growth depression and kidney lesions but some mortality has also been reported. One-day-old chicks are the birds most susceptible to disease caused by ANV.

Duck astrovirus (DAstV) has been shown to be the causal agent of duck hepatitis type 2 in ducks. The duck astrovirus was shown to be immunologically distinct from astroviruses isolated from chicken (ANV) and turkeys and from the viruses that cause DVH types I and III.

The present invention has identified a new (sub)type of avian astrovirus isolatable from chickens (CAstV-2) that is immunologically distinct from the known chicken astrovirus ANV (CAstV-1) and from other avian astroviruses.

Therefore, the present invention provides a chicken astrovirus type 2 (CAstV-2), characterised in that the virus is the Chicken Astrovirus VDU/AS2 deposited under accession no. 1-2932 at the Collection Nationale de Cultures de Microorganismes (CNCM) of the Institute Pasteur, 28, Rue du Docteur Roux, F-75724 Paris, France or an immunological related CAstV that is able to induce antiserum that neutralizes the deposited virus.

As mentioned-above, the existing avian astroviruses are immunologically distinct and the CAstV-2 as defined above has also been found to be immunologically distinguishable from previously known avian (astro)viruses. The new CAstV-2 can be used for the preparation of poultry vaccines and diagnostic tests. A CAstV-2 according to the invention can be obtained from the Depository Institute (CNCM of the Institute Pasteur) or can be isolated from infected animals in the field and can be identified as such by reaction with specific antisera raised against the deposited virus in an immunological assay as described in the Examples. A virus neutralization assay is particularly suitable for the identification of a CAstV-2 according to the present invention.

It is generally accepted that biological variation exists in nature between organisms of the same type. For the purpose of this invention the deposited CAstV is considered to be the reference strain of CAstV-2 with which the other CAstV-2 strains are immunologically related. The virus neutralization assay and immunofluorescence (IF) assay are widely used in the art for determining the presence or absence of an immunological relationship between (avian) viruses. Typical virus neutralization and IF assays are described in the Examples and are also disclosed in Mockett et al. (Avian Pathology 22, 751-770, 1993), McNulty et al. (Avian Pathology 19, 75-87, 1990) and Nersessian et al. (Am. J. Vet. Res. 50, 1475-1480, 1989). In Tables 1 and 2 it is shown that CAstV-2 strains form a homogeneous serogroup of chicken astroviruses that is immunological distinct from the known avian astroviruses.

Therefore, a CAstV is considered to belong to the present invention in case the avian astrovirus is immunological related to the deposited CAstV, that is to say in case it is able to induce antiserum that is capable of neutralizing the deposited virus in a virus neutralization assay. A neutralization assay that can be used to determine the immunological relationship is described in Example 2 below.

Obviously, the antiserum to be used in the virus neutralization assay should be of appropriate quality. Methods for the preparation of such antiserum are described in Example 2.

Generally, appropriate antiserum raised against a live CAstV can be prepared by inoculating 3 to 4 weeks old SPF chickens orally with a live virus strain having an infectious titre between $10^{2.0}$-$10^{9.0}$ pfu/animal; more preferably between $10^{3.0}$-$10^{6.0}$ pfu/animal. Blood can be collected 3 to 4 weeks after infection, preferably 4 weeks after infection. Chickens may also be re-infected with the same live virus strain 3 to 4 weeks after the first infection with approximately the same dose as used in the first infection. Blood is collected between 2 and 4 weeks after the second infection.

Appropriate antiserum raised against inactivated CAstV can be obtained by inoculating 3 to 4 weeks old SPF chickens subcutaneously or intramuscularly with the inactivated virus preparation and an adjuvant. The infectious titre of the preparation before inactivation may be between $10^{7.0}$-$10^{11.0}$ pfu/animal; more preferably between $10^{8.0}$-$10^{10.0}$ pfu/animal. Blood can be collected 3 to 4 weeks after inoculation, preferably 4 weeks after inoculation. Chickens may also be re-inoculated with the inactivated virus preparation 3 to 4 weeks after a first inoculation with the live- or inactivated virus preparation. Blood is collected between 2 and 4 weeks after the second inoculation.

An antiserum of appropriate quality typically comprises a neutralizing antibody titre of $\geq 256$ against the homologous virus.

Preferably, the present invention provides a chicken astrovirus type 2 (CAstV-2), characterised in that the virus is the CAstV deposited under accession no. I-2932 at the Collection Nationale de Cultures de Microorganismes (CNCM) of the Institute Pasteur, Paris, France or an immunological related CAstV that has a percent relatedness (% R) with the deposited virus of at least 32, more preferable at least 50, most preferably at least 70 as determined by virus cross-neutralisation and calculated according to the method of Archetti and Horsefall (J. Exp. Med. 92, 441-462, 1950). "R-values" of 32-50 between a test virus and the deposited CAstV indicate a clear immunological relationship between the two, whereas a "R-value" of 50-70 and at least 70 indicate minor or little/no immunological difference, respectively.

Further characterization of the CAstV-2:

Treatment with ether and IDUR: The virus is a stable agent resistant to ether and its growth was not inhibited by IDUR—indicating it is a RNA virus.

Immunofluorescent test: Infected cell cultures when tested using the immunofluorescent test show cytoplasmic fluorescence with no nuclear fluorescence. High antibody titre serum could be used at a dilution of >1:256 giving bright fluorescence.

Cross neutralization test: In a plaque reduction test the virus is neutralised well with antiserum induced against itself with serum titres greater than 512 often observed. Antisera against the following agents have shown no cross neutralisation.

a) Avian adenovirus (CELO, GAL, Tipton, EDS and HEV)
    b) Avian encephalomyelits virus (AE)
    c) Fowl, Turkey and Pigeon pox virus
    d) Infectious bursal disease virus
    e) Avian Pneumovirus (TRT)
    f) Retroviruses (Avian Leucosis and Reticulo-endotheliosis viruses)
    g) Avian reo-viruses
    h) Avian Nephritis virus
    i) Chick anaemia virus Electron microscopy: Suspension containing viral particles purified from infected cells was placed on carbon-coated copper grids and subjected to negative staining. Examination in an electron microscope revealed the presence of clusters of small-round viruses with a diameter ranging from 25-30 nm.

RT-PCR and Sequence determination: In order to obtain sequence information from the genome of the agent, total RNA was isolated from purified virus using the Rneasy kit (Qiagen). For an RT-PCR, two primers derived from a conserved region situated in ORF1 of small-round-structured virus (SRSV) genomes (Wyn-Jones et al., J. Virol. Methods 87, 99-107, 2000) were employed. The obtained PCR product was approximately 400 base pair (bp) in size and the nucleotide sequence determined from both directions (~320 bp) was compared to reported sequences in the GeneBank database using a basic local alignment search tool (BLAST). The putative amino acid sequences derived from the PCR product were identified as having moderate similarities to the non-structural polyproteins of turkey astrovirus 1 and 2 (62% identities), avian nephritis virus (55% identities) and sheep astroviruses (33% identities). This genetic information indicates that the agent is a chicken astrovirus belonging to the family Astroviridae.

As demonstrated in the Examples, the CAstV-2 according to the invention displays an immunogenic make-up that is not observed before. Therefore, the new CAstV-2 may form the basis of a new type of avian astrovirus vaccine that can effectively protect poultry against disease conditions resulting from the infection by the new CAstV-2. Hence, another aspect of this invention is a vaccine for use in the protection of poultry against disease caused by avian astrovirus infection, characterised in that the vaccine comprises a CAstV-2 as defined above, together with a pharmaceutical acceptable carrier or diluent.

The CAstV-2 according to the invention can be incorporated into the vaccine as a live attenuated or inactivated virus.

A vaccine according to the invention can be prepared by conventional methods such as for example those commonly used for the preparation of commercially available live- and inactivated vaccines derived from viruses pathogenic for poultry, such as Infectious bronchitis virus, marek's disease virus and infectious bursal disease virus (Veterinary Vaccinology, eds.:Pastoret et al., Elsevier, Amsterdam, 1997).

Briefly, a susceptible substrate is inoculated with a CAstV-2 according to the invention and propagated until the virus replicated to a desired infectious titre after which CAstV-2 containing material is harvested, optionally inactivated, and mixed with a pharmaceutical acceptable carrier or diluent.

Every substrate which is able to support the replication of CAstV-2 can be used to prepare a vaccine according to the present invention, including primary (avian) cell cultures, such as chicken embryo fibroblast cells (CEF) or chicken embryo liver cells (CEL). Usually, cells are incubated at 39° C. and can be infected after 24-48 hours at which time the medium is removed from the cultures and the virus inoculated onto the culture and allowed to absorb for 20-40 minutes. Fresh medium is used to refeed the culture, which is then incubated for a further 24-96 hours. At this time the infected cell culture fluids and the infected cells may be harvested separately or together. In order to liberate cell-associated virus the infected cells are sonicated for 3×5 seconds. If desired cell debris may be removed by filtration or centrifugation.

Therefore, in a further embodiment the present invention provides a cell culture infected with a CAstV-2 as defined above.

The new CAstV-2 can also be propagated in embryonated chicken eggs.

Attenuation of the CAstV-2 can be obtained by standard serial passaging of the virus in cell cultures, for example in primary cell cultures (e.g. CEL cell culture) or established cell lines that support the replication of the virus. In this case, passage levels between 5-150, preferably between 20-50, may be used. Obviously, also naturally occurring attenuated strains of the new CAstV-2 may be used for the preparation of a live vaccine.

The vaccine according to the invention containing the live virus can be prepared and marketed in the form of a suspension or in a lyophilised form and additionally contains a pharmaceutically acceptable carrier or diluent customary used for such compositions. Carriers include stabilisers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are the same as mentioned below for an inactivated vaccine.

Although administration by injection, e.g. intramuscularly, subcutaneously or in ovo of the live vaccine according to the present invention is possible, the vaccine is preferably administered by an inexpensive mass application route commonly used for poultry vaccination. For CAstV-2 vaccination this route includes drinking water, spray and aerosol vaccination.

Alternatively, the present invention provides a vaccine comprising the new CAstV-2 in an inactivated (killed) form.

The aim of inactivation of the viruses harvested after the propagation step is to eliminate reproduction of the viruses. In general, this can be achieved by chemical or physical means well known in the art. Formaldehyde and β-propiolactone are suitable inactivating agents.

A vaccine containing the inactivated CAstV-2 can, for example, comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

The vaccine according to the invention comprises an effective dosage of the CAstV-2 as the active component, i.e., an amount of immunising CAstV-2 material that will induce immunity in the vaccinated birds against challenge by a virulent virus. Immunity is defined herein as the induction of a statistically significant higher level of protection in a population of birds after vaccination compared to an unvaccinated group.

Typically, the live vaccine according to the invention can be administered in a dose of $10^1$-$10^6$ plaque forming units (pfu) per animal (1 ml dose), preferably in a dose ranging from $10^3$-$10^5$ pfu per animal. Inactivated vaccines may contain the antigenic equivalent of $10^6$-$10^{10}$ pfu per animal.

Inactivated vaccines are usually administered parenterally, e.g. intramuscularly or subcutaneously.

Although, the CAstV-2 vaccine according to the present invention may be used effectively in chickens, also other poultry such as turkeys may be successfully vaccinated with the vaccine. Chickens include broilers, pullets, reproduction stock and laying stock.

It is possible to induce an antibody response by vaccinating parent stock (e.g. at 12-16 weeks of age for broiler breeder stock) with or without prior vaccination with the CAstV-2 vaccine as young stock. The antibodies induced by such a vaccination regime are high and are passed through to the progeny in the yolk to provide protection against early challenge with field astrovirus. It is also possible to vaccinate young birds, in particular with a live attenuated vaccine, early in life, preferably at day-old, to induce active immunity.

The invention also includes combination vaccines comprising, in addition to the CAstV-2 described above, one or more vaccine components of other pathogens infectious to poultry.

Preferably, the combination vaccine additionally comprises one or more vaccine strains of Mareks Disease virus (MDV), infectious bronchitis virus (IBV), Newcastle disease virus (NDV), egg drop syndrome (EDS) virus, turkey rhinotracheitis virus (TRTV) or reovirus.

A CAstV-2 according to the invention can also be used for the preparation of diagnostic assays. The CAstV-2 can be used as an antigen in immuno assays for the detection of CAstV-2 antibodies in samples of animals suspected of being infected by that virus. Alternatively, the CAstV-2 can be used to raised antisera to be used in a diagnostic assay, i.e. for the detection of CAstV-2 antigen.

DETAILED DESCRIPTION OF THE INVENTION

Examples

Example 1

Isolation of CAstV-2 Strains

CAstV-2—VDU/As1

Tracheal and vent swabs taken from 10 broiler chicks (5 days old) with diarrhea were washed with PBS and the total volume (0.2 ml) of fluid from each sample was inoculated on to CEL cultures. After 6 days an astrovirus induced cytopathic effect was observed in the cultures inoculated with one of the tracheal swab samples. Reovirus and adenovirus was isolated from the other samples. This astrovirus was plaque-purified three times, a single plaque being taken from a plate with less than 10 plaques on it.

CAstV-2—VDU/As2

Ten, 1 ml heparinised blood samples were taken from one-week-old broiler chicks that showed uneven growth. The white blood cells were separated from the samples after centrifugation (using a bench centrifuge) and approximately 0.1 ml of packed white cells were inoculated into the medium of each of two 48 hours old chick embryo liver (CEL) 6 cm cell culture tissue plates.

After 24 hours incubation in 5% $CO_2$ atmosphere at 37° C. the white cells together with the medium were poured off the cell cultures. The cultures were washed with phosphate buffered saline (PBS) and this maintenance medium replenished.

After a further 6 days incubation an astrovirus induced cytopathic effect was observed in two of the cultures inoculated with the white blood cells, no other virus being isolated.

CAstV-2—VDU/As3

The virus was isolated from a pool of small intestines (homogenized) (SI) from three 3-week-old chicks with diarrhea. The SI samples were filtered using a coarse filter and diluted 100-fold with PBS containing 5× normal cell culture levels of penicillin and streptomycin. The samples were centrifuged (bench centrifuge) to remove particulate debris and then the supernatant was diluted in 10-fold steps to $10^{-6}$ and each dilution inoculated onto four CEL plates. After absorption for 40 minutes plates were overlaid with medium containing 0.9% agar and two refeed with normal fluid maintenance medium.

Four days later typical reovirus plaques and CPE were observed in dilutions up to $10^{-3}$.

A single plaque was observed in one plate at the $10^{-4}$ dilution. This plaque was picked and inoculated onto fresh CEL cultures where a typical astrovirus CPE developed by 5 days. The virus was plaque-picked on two further occasions before a pool of virus was laid down.

Harvesting of CEL Culture Infected with the Virus:

The supernatant cell culture fluids of CEL cultures showing a cytopathic effect were removed and frozen at −70° C.

The CEL cells were removed from the plates using a rubber policeman and then frozen at −70° C.

When titrated using a plaque titration assay both the supernatant and the cells contained viruses. The titre within the cells was usually >10-fold higher than those in the supernatant fluids.

A sample of the CAstV-2 strain VDU/As2 was deposited at the Collection Nationale de Cultures de Microorganismes of the Institute Pasteur, Paris, France (28, Rue du Docteur Roux, F-75724 Paris Cedex 15) under accession no. I-2932 on Sept. 13, 2002.

Example 2

Immunological Characterization of CAstV-2

Materials and Methods

Production of Specific Antisera

10×2-week-old SPF chicks (White Leghorn) were inoculated with $10^6$ pfu/chick of live CAstV-2 orally. After a further 4 weeks each chick was inoculated subcutaneously with $10^9$ pfu of CAstV-2 mixed with incomplete Freudts adjuvant (Vol 0.5 ml/chick).

Blood was collected 4 weeks after the last inoculation and the serum separated and stored at $-20°$ C. The serum neutralizing titres varied between 256 and 1024. Sera against other avian astroviruses were prepared according to similar protocols.

Virus Neutralisation Assay

The plaque reduction test was used for CAstV-2, ANV (except for the ANV experiment described in Table 1b), TastV and DVH-2 antibody test. Antisera were diluted with phosphate buffered saline in two-fold steps. An equal volume of each antiserum dilution (usually 0.5 ml) was mixed with an equal volume of a virus preparation diluted to contain approximately 200 plaque forming units 0.1 ml.

The antiserum/virus mixtures were incubated for 40 minutes at room temperature (20-22° C. before 0.1 ml of each dilution is inoculated onto each of two 6 cm 48 hour old confluent chick embryos cell culture petri dishes that have had the medium removed.

After absorption for 40 mins at 38.5° C. the cultures were overlaid with eagles maintenance medium containing 1% Bacto agar.

The cultures were incubated at 38.5° C. in a 5% $CO_2$ atmosphere for 5 days at which time 2 ml of Neutral Red solution is added to each plate.

The plaques were counted 24 hours later and viewed using incident light or against a white background.

The mean plaque count of the two plates inoculated with each virus/antiserum dilution is used to calculate the percentage of virus plaque forming units surviving neutralisation as compared with a virus control and a control negative serum.

The antiserum titre is expressed as the reciprocal of that antiserum dilution nearest to giving 75% reduction of plaques as compared with the negative control serum. All serum titres are given as final dilution after the addition of the equal volume of virus.

The microtitre neutralisation test was used for the ANV antibody test described in Table 1 b. Two fold dilutions of serum were mixed with an equal volume of virus diluted in MEM to give 200 tissue culture infective doses (TCID)/0.1 ml. Following incubation at room temperature for 1 hr 0.1 ml from each dilution was placed into four microtitre in a 96 well plate well and 0.1 ml of growth medium and $3\times10^4$ cells added to each well. A virus titration and negative serum was included in each test. The plates were incubated for 5 days at 38.5° C. in a CO2 atmosphere and then read microscopically. The serum titre was the dilution where only 50% of wells showed a CPE.

Immunofluorescence Test (IFT)

Susceptible cells were grown in 24-well plates. When confluent they were infected with the virus. The infected cultures were fixed between 12 and 18 hours post-inoculation with 100% meths for 1 hour and then poured off. When the meths has evaporated a small volume of chick anti-serum was placed onto the fixed cells (enough to cover the cell sheet). This was then incubated at 38.5° C. for 45 minutes. The cell sheet was then washed 3-5 times with PBS. A small volume of the appropriate rabbit IgG whole molecule FITC conjugate was then placed onto the cell sheet (enough to cover the cell sheet) at the required dilution. This was then incubated at 38.5° C. for a further 45 minutes. The cell sheet was then washed again (3-5 times). Finally a 50:50 mixture of PBS: Glycerol was added (enough to cover cell sheet). The vessel is stored in the dark at +4° C. until it is viewed with a fluorescence microscope. Infected cells display cytoplasmic fluorescence.

Gel Diffusion Test

Before use in a gel diffusion test a pool of antigen was concentrated by freeze-thawing infected cell suspension and adding equal volume of saturated ammonium sulphate, followed by (o/n) precipitation and centrifugation. Concentrated antigen is dialysed in a container of PBS.

Antigen was placed in the central well (2% Agarose gel) with test sera in the surrounding wells, and incubate overnight at 37° C. in a humidified container.

If a positive antibody reaction has taken place, a line of precipitation can be seen between the antigen well and the antiserum well.

Results

TABLE 1a

Immunological relationship between avian astroviruses CAstV-2, ANV and TastV

| | | | VIRUS | | |
|---|---|---|---|---|---|
| | | | CAstV-2 (VDU/AS2) | ANV | TastV (strain TEV) |
| ANTI-SERA | VDU/AS1 (VDU/AS2) | Neutralization | 256* | <16 | ND |
| | | Immunofluorescence | 128 | <8 | ND |
| | | Gel Diffusion | + | – | ND |
| | ANV | Neutralization | <16 | 256 | ND |
| | | Immunofluorescence | <16 | 32 | ND |
| | | Gel Diffusion | – | + | ND |
| | TastV (strain TEV) | Neutralization | <16 | ND | ND |
| | | Immunofluorescence | <16 | ND | ND |

TABLE 1b

Immunological relationship between avian astroviruses CAstV-2, ANV and DVH-2

| | | | VIRUS | | |
|---|---|---|---|---|---|
| | | | CAstV-2 (VDU/AS1) | ANV | DVH-2 |
| ANTI-SERUM | CAstV-2 (VDU/AS1) | Neutralization | 1600* | <10 | <10 |
| | | Immunofluorescence | 256 | <10 | <10 |
| | | Gel Diffusion | + | – | – |
| | ANV | Neutralization | <10 | 2048 | <10 |
| | | Immunofluorescence | <10 | 64 | <10 |
| | | Gel Diffusion | – | + | – |
| | DVH-2 | Neutralization | <10 | <10 | 1600 |
| | | Immunofluorescence | <10 | <10 | 128 |
| | | Gel Diffusion | – | – | + |

Key
* = serum titre
– = Negative reaction
+ = Positive reaction
ND = Not done

TABLE 2

Immunological relationship between CAstV-2 strains

| | | | VIRUS | | |
|---|---|---|---|---|---|
| | | | VDU/AS1 | VDU/AS2 | VDU/AS3 |
| ANTI-SERA | VDU/AS1 | Neutralization | 256* | 128 | 256 |
| | | Immunofluo-rescence | 64 | 64 | 64 |
| | | Gel Diffusion | + | + | + |
| | VDU/AS2 | Neutralization | 128 | 128 | 256 |
| | | Immunofluo-rescence | 32 | 32 | 32 |
| | | Gel Diffusion | + | + | + |
| | VDU/AS3 | Neutralization | 256 | 512 | 512 |
| | | Immunofluo-rescence | 128 | 128 | 128 |
| | | Gel Diffusion | + | + | + |

Key
* = serum titre
+ = Positive reaction

The results depicted in these Tables demonstrate on, the one hand, that CAstV-2 strains form a homogeneous group of immunologically related viruses and, on the other hand, that that CAstV-2 is immunologically distinct from the other avian astroviruses.

Example 3

Pathogenicity Test in Young Chicks

Twenty, day-old SPF chicks were inoculated with $10^{5.6}$ plaque forming units (PFU) of an isolate from strain CAstV-2 strain a. The virus had been plaque-picked three times from a $10^{-4}$ dilution of the virus and had undergone a total of 6 CEL culture passages.

All inoculated chicks showed diarrhea and passed partly digested food in feces. When 4 chicks were killed 5 days after infection they all showed some degree of distended small intestines.

The 17 control uninfected chicks showed no such signs and when 5 were killed at 5 days the intestines appeared normal.

The invention claimed is:

1. A chicken astrovirus type 2 (CAstV-2), characterised in that the virus is the CAstV deposited under accession no. I-2932 at the Collection Nationale de Cultures de Microorganisms (CNCM) of the Institute Pasteur, Paris, France or a CastV-2 that is able to induce antiserum having a neutralizing antibody liter greater than or equal to 128 against the deposited virus as measured in a virus neutralization assay and greater than or equal to 32 as measured in an immunofluorescence assay.

2. An immunogenic composition comprising a CAstV-2 according to claim 1, together with a pharmaceutically acceptable cater or diluent.

3. The immunogenic composition according to claim 2, characterized in the CAstV-2 is in a live attenuated form.

4. The immunogenic composition of claim 2, further comprising one or more vaccine components of other pathogens infectious to poultry.

5. The immunogenic composition according to claim 2, further comprising an adjuvant.

6. A method for the preparation of CAstV-2 antigen material, wherein a CAstV-2 according to claim 1 is propagated in a cell culture and subsequently harvested from the cell culture.

7. A method for the preparation of a vaccine according to claim 2, an immunogenic composition, wherein a CAstV-2 according to claim 1 is mixed with a pharmaceutical pharmaceutically acceptable carrier or a diluent.

8. A method for raising an immune response in poultry, against avian astrovirus, comprising administering an immunogenic composition according to claim 2 to poultry.

* * * * *